US010385952B2

(12) United States Patent
Tsuchiya et al.

(10) Patent No.: US 10,385,952 B2
(45) Date of Patent: Aug. 20, 2019

(54) ROTATING CYLINDER DEVICE (71) Applicants: SINTAI OPTICAL (SHENZHEN) CO., LTD., Shenzhen, Guandong Province (CN); ASIA OPTICAL INTERNATIONAL LTD., Tortola (VG)

(72) Inventors: Chikashi Tsuchiya, Taichung (TW); Naofumi Imai, Taichung (TW)

(73) Assignees: SINTAI OPTICAL (SHENZHEN) CO., LTD., Shenzhen, Guandong Province (CN); ASIA OPTICAL INTERNATIONAL LTD., Tortola (VG)

( * ) Notice: Subject to any disclaimer, the term of this patent is extended or adjusted under 35 U.S.C. 154(b) by 431 days.

(21) Appl. No.: 15/284,293

(22) Filed: Oct. 3, 2016

(65) Prior Publication Data
US 2017/0184189 A1 Jun. 29, 2017

(30) Foreign Application Priority Data
Dec. 25, 2015 (TW) .............................. 104143745 A (51) Int. Cl.
*F16H 37/12* (2006.01)
*A61B 5/00* (2006.01)
(Continued)

(52) U.S. Cl.
CPC ......... *F16H 37/12* (2013.01); *A61B 5/02141* (2013.01); *A61B 5/02233* (2013.01);
(Continued)

(58) Field of Classification Search
CPC ........ F16H 37/12; F16H 19/001; F16H 21/54; F16H 25/18; A61B 5/02141; A61B 5/02233
See application file for complete search history.

(56) References Cited

U.S. PATENT DOCUMENTS 3,218,937 A * 11/1965 Dettlof ..................... B62D 3/00
74/57
4,206,765 A * 6/1980 Huber ................ A61B 5/02141
600/490

(Continued)

OTHER PUBLICATIONS

EP Search Report dated Jun. 6, 2017 in European application (No. 16191661.4-1657).

*Primary Examiner* — David M Fenstermacher
(74) *Attorney, Agent, or Firm* — McClure, Qualey & Rodack, LLP (57) ABSTRACT A rotating cylinder device includes a cylindrical belt having an axis line, several plate-shaped parts, several link mechanisms, and a cylindrical casing. The plate-shaped parts are disposed outside the belt and arranged symmetrically across the axis line. The link mechanisms are pivotally connected to the respective plate-shaped parts and each have a moving protrusion. The moving protrusions are adapted to move along a first direction parallel to the axis line. The cylindrical casing is adapted to rotate about the axis line and is coupled to the moving protrusions. When the cylindrical casing rotates about the axis line, the moving protrusions are driven to move along the first direction, and the plate-shaped parts are driven by the link mechanisms to move along a second direction perpendicular to the axis line, to contract the belt.

17 Claims, 8 Drawing Sheets (51) Int. Cl.
*A61B 5/021* (2006.01)
*A61B 5/022* (2006.01)
*F16H 19/00* (2006.01)
*F16H 21/54* (2006.01)
*F16H 25/18* (2006.01)

(52) U.S. Cl.
CPC ........... *A61B 5/702* (2013.01); *F16H 19/001* (2013.01); *F16H 21/54* (2013.01); *F16H 25/18* (2013.01)

(56) References Cited

U.S. PATENT DOCUMENTS

| | | | | |
|---|---|---|---|---|
| 4,355,545 | A * | 10/1982 | Ross | D05B 65/00 74/567 |
| 4,725,260 | A * | 2/1988 | Komorowski | F16H 7/1218 474/135 |
| 5,873,335 | A * | 2/1999 | Wright | F01L 9/04 123/198 D |
| 7,237,449 | B2 * | 7/2007 | Kato | B23Q 1/58 74/25 |
| 8,534,151 | B2 * | 9/2013 | Johnson | F16D 11/10 399/167 |
| 2003/0070633 | A1 * | 4/2003 | Al Hawaj | F02B 75/26 123/56.1 |
| 2003/0109771 | A1 * | 6/2003 | Forsell | A61F 2/26 600/38 |
| 2004/0044288 | A1 * | 3/2004 | Gorenberg | A61B 5/02141 600/481 |
| 2004/0142781 | A1 * | 7/2004 | Huddleston | F16H 55/56 474/19 |
| 2004/0255627 | A1 * | 12/2004 | Shimon | E05B 17/0058 70/379 R |
| 2005/0240109 | A1 * | 10/2005 | Inoue | A61B 5/021 600/499 |
| 2007/0260245 | A1 * | 11/2007 | Malandain | A61B 17/025 606/250 |
| 2011/0125036 | A1 * | 5/2011 | Nakajima | A61B 5/0285 600/500 |
| 2012/0123196 | A1 | 5/2012 | Rion et al. | |
| 2014/0187987 | A1 * | 7/2014 | Fraden | A61B 5/02233 600/499 |
| 2017/0224357 | A1 * | 8/2017 | Whalen | A61B 17/1204 |
| 2017/0312165 | A1 * | 11/2017 | Johnson | A41D 1/005 |
| 2018/0021210 | A1 * | 1/2018 | Stray-Gundersen | A61H 9/0092 601/152 |

* cited by examiner

ROTATING CYLINDER DEVICE

CROSS REFERENCE TO RELATED APPLICATIONS

The present application claims priority of Taiwan Patent Application No. 104143745, filed on Dec. 25, 2015, the entirety of which is incorporated by reference herein.

BACKGROUND OF THE INVENTION

Field of the Invention

The present application relates to a rotating cylinder device, and in particular to a wrap belt mechanism of a rotating cylinder device.

Description of the Related Art

A blood pressure monitor is a medical device which measures blood pressure.

When using a blood pressure monitor, an arm belt will be wrapped around the arm of a patient. In the process of increasing the pressure in the arm belt to exceed the maximum blood pressure and then being decreased gradually, the arterial pulsation in the arm can be detected by a pressure sensor via the arm belt, and thus the maximum and minimum blood pressure can be determined.

However, with regard to the arm belts of traditional blood pressure monitors, there is a problem in that the pressure applied around the patient's arm is usually inconsistent. This affects not only the comfort of the patient but also the accuracy of the results of the blood pressure measurement.

BRIEF SUMMARY OF THE INVENTION

In view of the aforementioned problems, an object of the invention is to provide a rotating cylinder device in which the belt can be contracted and wrapped in a uniform manner, so that the pressure applied around the patient's arm is more consistent.

An embodiment of the invention provides a rotating cylinder device, including a belt, several plate-shaped parts, several link mechanisms, and a cylindrical casing. The belt is substantially cylindrical and has an axis line. The plate-shaped parts are disposed outside the belt and arranged symmetrically across the axis line. The link mechanisms are pivotally connected to the respective plate-shaped parts, wherein one end of each of the link mechanisms is pivotally connected to one of the plate-shaped parts and the other end is provided with a moving protrusion. The moving protrusions of the link mechanisms are adapted to move along a first direction parallel to the axis line. The cylindrical casing is adapted to rotate about the axis line and coupled to the moving protrusions. When the cylindrical casing rotates about the axis line, the moving protrusions are driven to move along the first direction, and the plate-shaped parts are driven by the link mechanisms to move along a second direction perpendicular to the axis line to contract the belt.

In an embodiment, when the plate-shaped parts move along the second direction, the plate-shaped parts go from an expanded state to a contracted state, and the plate-shaped parts are far from the axis line in the expanded state and are close to the axis line in the contracted state.

In an embodiment, the rotating cylinder device further includes a cylindrical frame disposed between the cylindrical casing and the plate-shaped parts, wherein the moving protrusions pass through the cylindrical frame and are coupled to the cylindrical casing.

In an embodiment, the other end provided with the moving protrusion of each of the link mechanisms is movably connected to the cylindrical frame.

In an embodiment, the cylindrical frame has a plurality of guide tracks thereon for guiding the moving protrusions as they move along the first direction.

In an embodiment, the cylindrical casing has a plurality of oblique grooves thereon, the oblique grooves being coupled to the moving protrusions, and the extension directions of the oblique grooves are different from those of the guide tracks.

In an embodiment, an auxiliary link is further provided between both ends of each of the link mechanisms, and both ends of the auxiliary link are coupled to the link mechanism and the cylindrical frame.

In an embodiment, the belt comprises a strengthened sheet.

In an embodiment, the rotating cylinder device further includes a driving element for driving the cylindrical casing to rotate about the axis line.

In an embodiment, the rotating cylinder device further includes a driving gear set connected to the driving element and a gear structure on a surface of the cylindrical casing.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

In order to illustrate the purposes, features, and advantages of the invention, the preferred embodiments and drawings of the invention are shown in detail as follows.

In the following detailed description, the orientations of "upper", "lower", "left", and "right" are used for representing the relationship between the relative positions of each element as illustrated in the drawings, and are not meant to limit the invention.

In addition, some elements not shown or described in the embodiments have the forms known by persons skilled in the field of the invention.

Figure 1A:
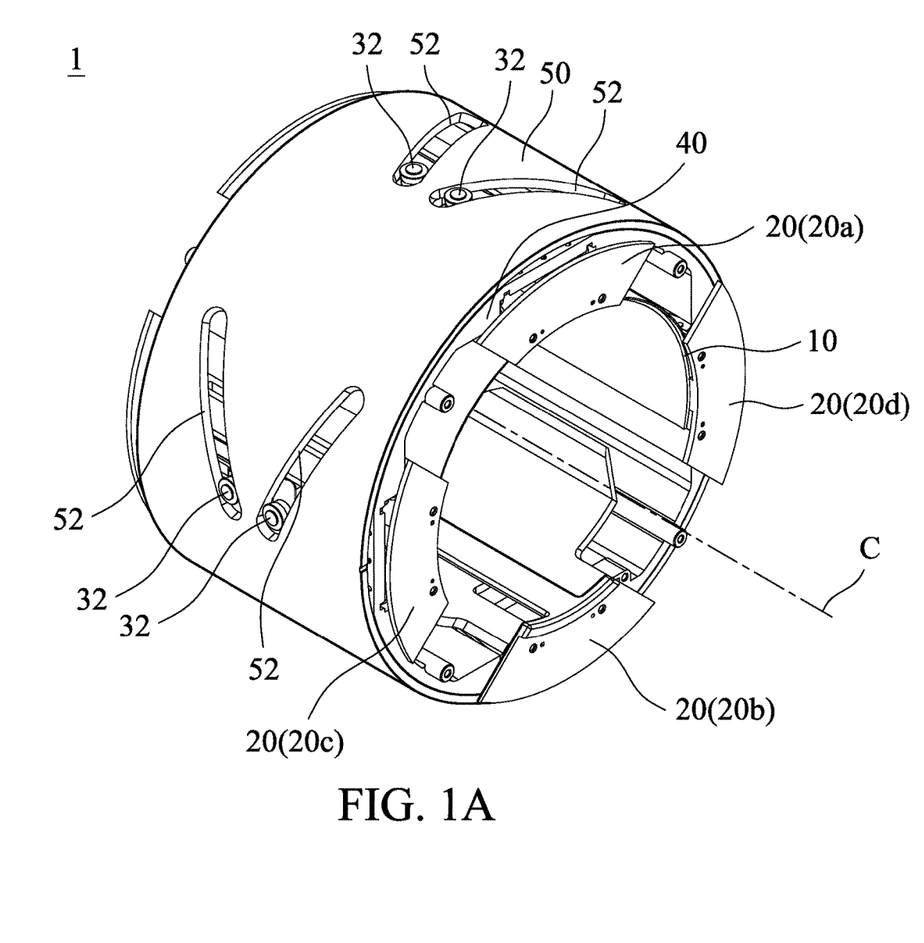
FIG. 1A and FIG. 1B are schematic views showing a belt of a rotating cylinder device in accordance with an embodiment of the invention being in a spread state and in a contracted state.
Figure 1B:
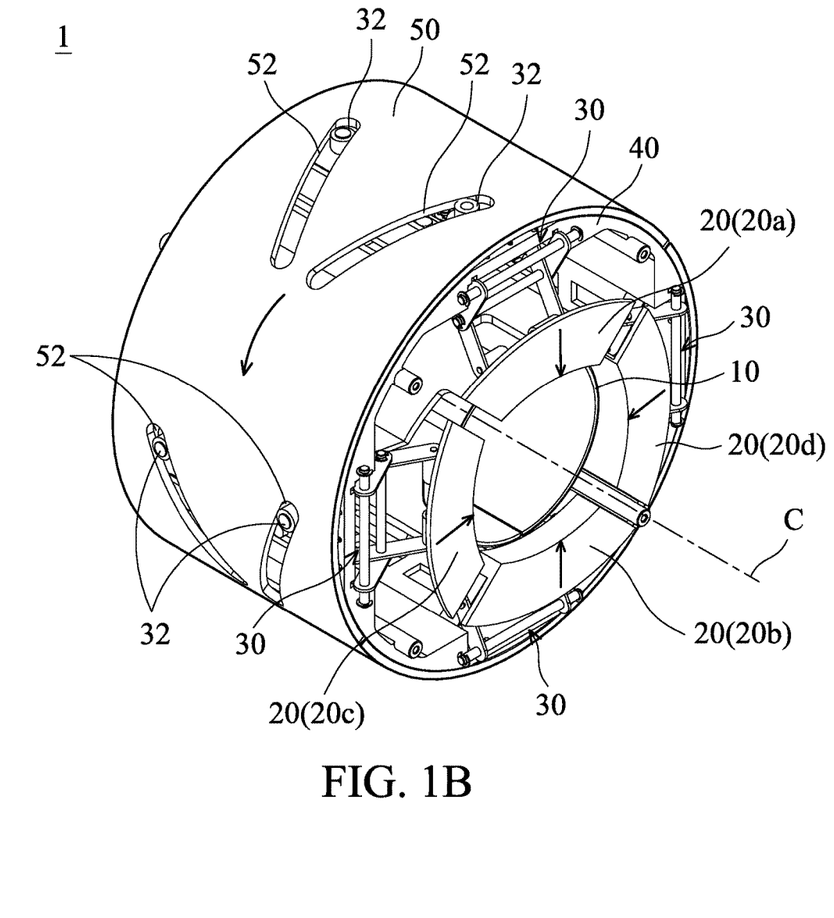

Referring to FIG. 1A and FIG. 1B, a rotating cylinder device 1 in accordance with an embodiment of the invention includes a belt 10, several plate-shaped parts 20 (including an upper plate-shaped part 20a, a lower plate-shaped part 20b, a left plate-shaped part 20c, and a right plate-shaped part 20d), several link mechanisms 30, a cylindrical frame 40, and a cylindrical casing 50.

The belt 10 is substantially cylindrical (the term "substantially" used here represents that the belt 10 of this embodiment is not a complete and continuous cylindrical structure) and has an axis line C located in the center of the rotating cylinder device 1. The belt 10 is used to wrap around the arms of the patients so as to take the subsequent blood pressure measurement. For example, the patient can place his arm into a soft arm sleeve (it may be provided in the center of the rotating cylinder device 1 and at inner side of the belt 10 (not shown)) in the rotating cylinder device 1, and then start the rotating cylinder device 1 to make the belt 10 move from a location far from the axis line C (i.e. a spread state, see FIG. 1A) to another location close to the axis line C (i.e. a contracted state, see FIG. 1B) so that the belt 10 is wrapped tightly around the patient's arm. Afterward, air is injected into the belt 10 (i.e. to compress the belt) through an inflation tube 14 (see FIG. 5) connected with the belt 10, and then the blood pressure measurement is started.

In this embodiment, the belt 10 comprises a strengthened sheet.

Figure 2A:
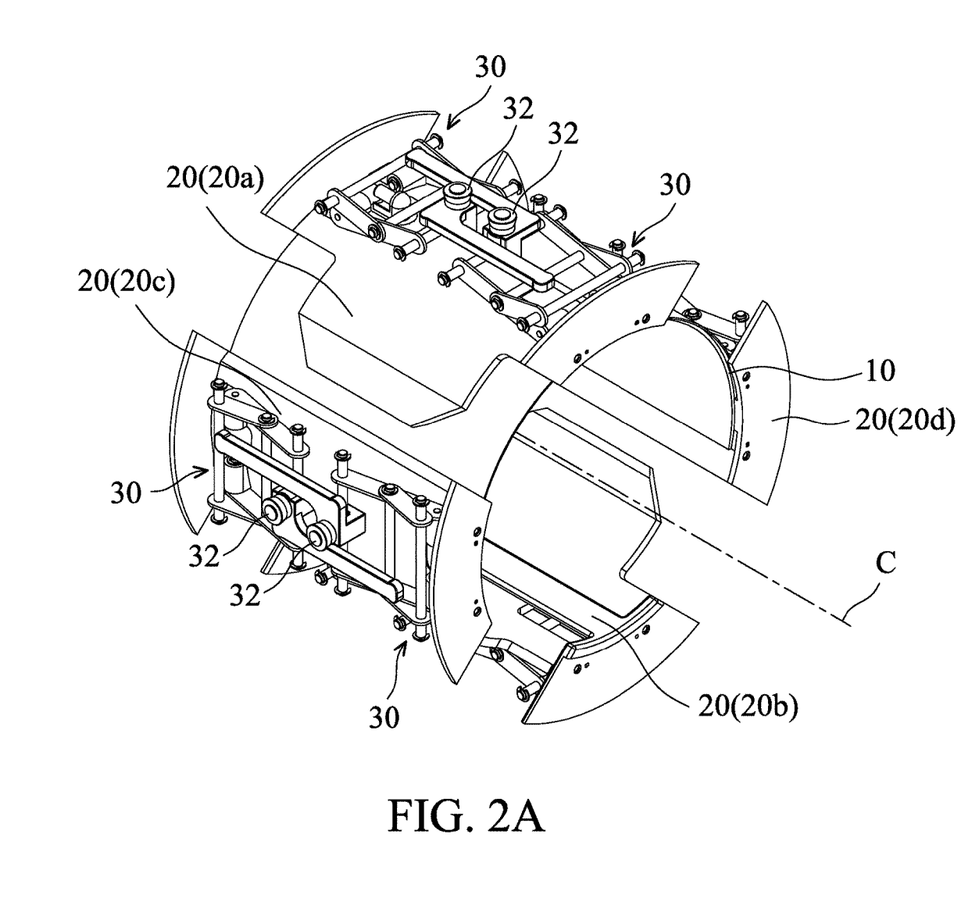
FIG. 2A and FIG. 2B are schematic views showing some parts of the rotating cylinder device in FIG. 1A and FIG. 1B, respectively.
Figure 2B:
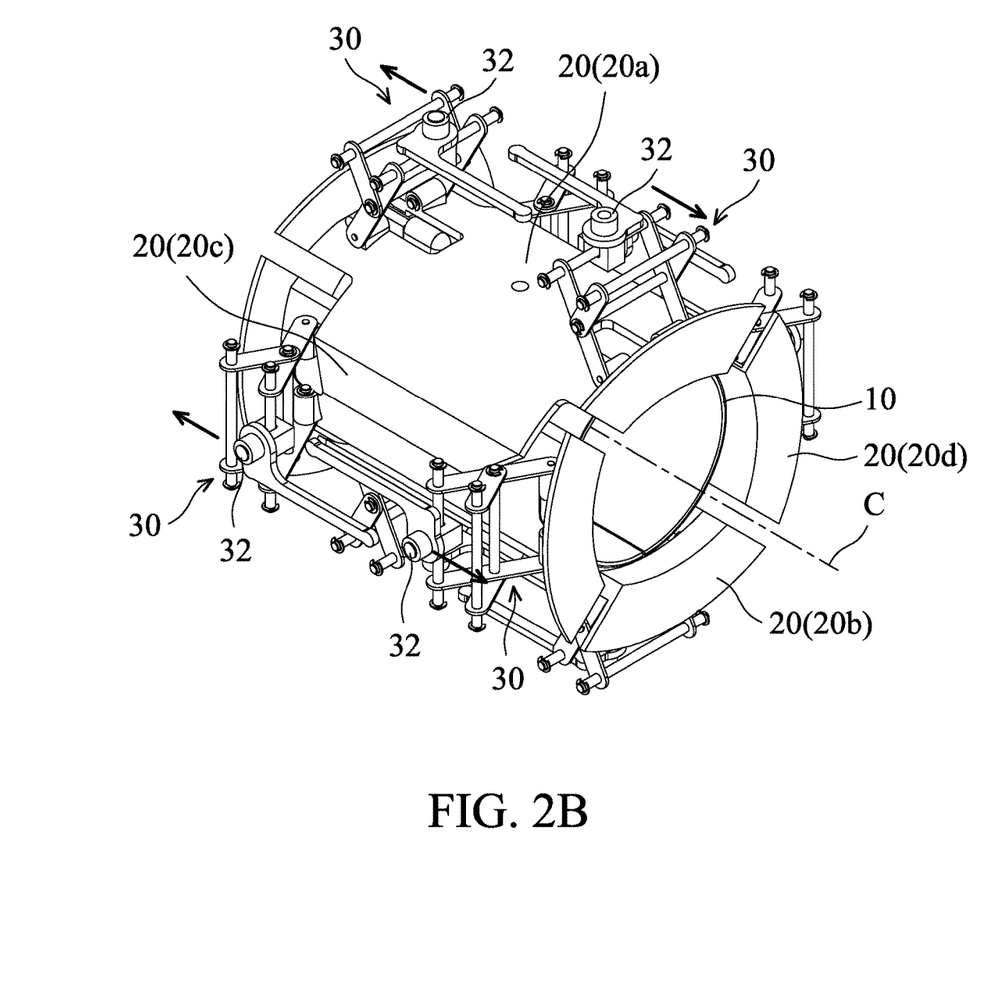

The (four) plate-shaped parts 20 are disposed outside the belt 10 and arranged symmetrically across the axis line C and are used to support the belt 10. Moreover, the plate-shaped parts 20 are adapted to move along a direction perpendicular to the axis line C (i.e. the radial direction of the cylindrical belt 10 (the second direction)) from an expanded state to a contracted state. Referring to FIG. 2A and FIG. 2B together, in this embodiment, each plate-shaped part 20 is a curved plate structure (corresponding to the shape of the belt 10). When the plate-shaped parts 20 are in the expanded state (see FIG. 2A), they are far from the axis line C so that the belt 10 is in a spread state. Conversely, when the plate-shaped parts 20 transition from the expanded state to the contracted state (see FIG. 2B), they are close to the axis line C so that the belt 10 is in a contracted state (the diameter of the belt 10 is reduced) and is wrapped tightly around the patient's arm.

As shown in FIG. 2A and FIG. 2B, the (eight) link mechanisms 30 are respectively disposed on the four plate-shaped parts 20 and are arranged so that two of the link mechanisms 30 are disposed on opposite sides of each of the plate-shaped parts 20. Specifically, one end of each of the link mechanisms 30 is pivotally connected to one of the plate-shaped parts 20 and the other end is provided with a moving protrusion 32. In this embodiment, the moving protrusions 32 of the link mechanisms 30 are adapted to move along a direction parallel to the axis line C (as indicated by the arrow in FIG. 2B, i.e. the first direction) toward opposite sides of the plate-shaped parts 20. Also, when the moving protrusions 32 move along the first direction, the plate-shaped parts 20 can be driven by the link mechanisms 30 to move along the direction perpendicular to the axis line C (the second direction). This driving mechanism will be further illustrated in the following description.

Referring to FIG. 1A to FIG. 3, the cylindrical frame 40 and the cylindrical casing 50 are disposed outside the belt 10, the plate-shaped parts 20 and the link mechanisms 30. The cylindrical casing 50 is further disposed outside the cylindrical frame 40 (i.e. the cylindrical frame 40 is disposed between the cylindrical casing 50 and the plate-shaped parts 20) and is adapted to rotate about the axis line C (as indicated by the arrow in FIG. 1B).

Figure 3:
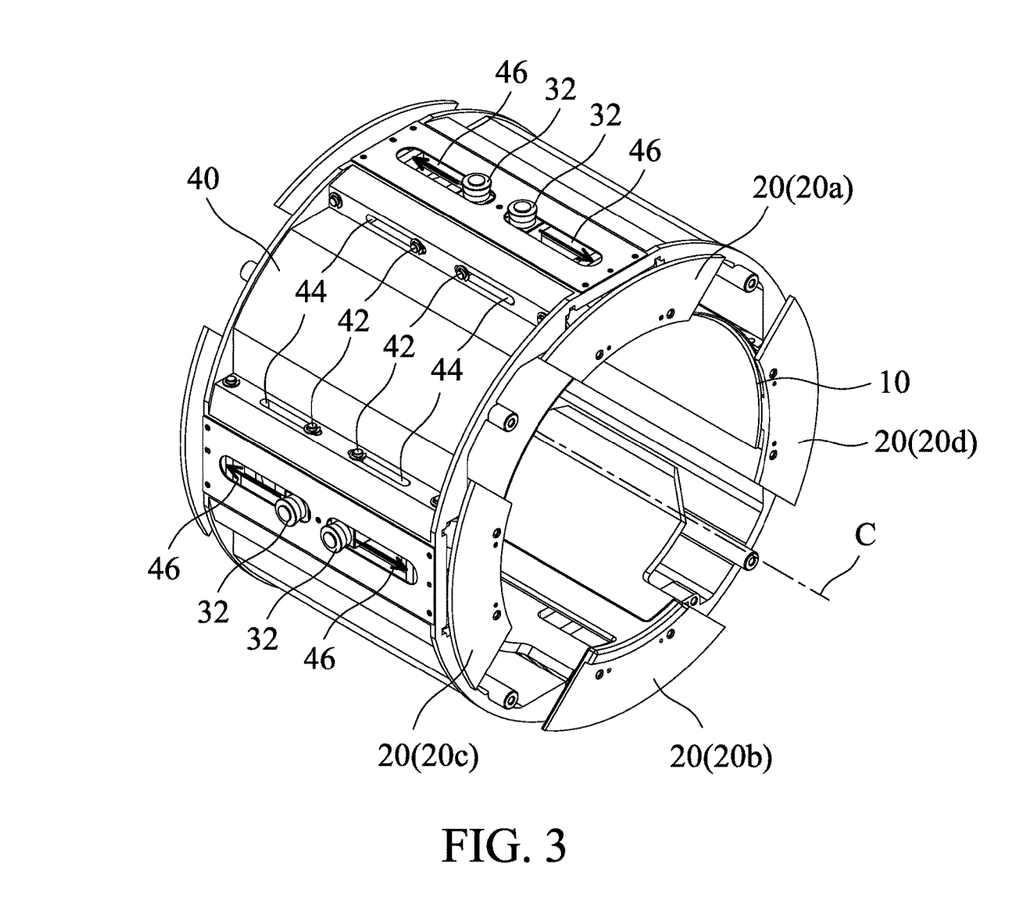
FIG. 3 is a schematic view showing some parts of the rotating cylinder device in FIG. 1A.

In this embodiment, the one end provided with the moving protrusion 32 of each link mechanism 30 is movably connected to the cylindrical frame 40 (in the locations indicated by reference number 42 in FIG. 3) and can move along the direction parallel to the axis line C (the first direction) within the tracks 44 on the cylindrical frame 40. The cylindrical frame 40 is used to support the link mechanisms 30. The moving protrusions 32 of the link mechanisms 30 further pass through the cylindrical frame 40 (i.e. exposed to the outside of the cylindrical frame 40, as shown in FIG. 3) and are coupled to several oblique grooves 52 on the cylindrical casing 50. Moreover, the cylindrical frame 40 further has several guide tracks 46 (the extension directions thereof are parallel to the direction of the axis line C) thereon for guiding the moving protrusions 32 of the link mechanisms 30 to move along the first direction (as indicated by the arrows in FIG. 3). Specifically, the extension directions of the oblique grooves 52 on the cylindrical casing 50 are different from those of the guide tracks 46 on the cylindrical frame 40 (i.e. the oblique grooves 52 and the guide tracks 46 therebetween form an angle which is not 0 degrees).

Referring to FIG. 1A to FIG. 4B, with the above structural design, when the cylindrical casing 50 rotates about the axis line C of the belt 10 (i.e. when starting the rotating cylinder device 1), the moving protrusions 32 of the link mechanisms 30 can be driven by the oblique grooves 52 on the cylindrical casing 50 and guided by the guide tracks 46 on the cylindrical frame 40 to move along the direction parallel to the axis line C (the first direction) with respect to the cylindrical frame 40. At the same time, the link mechanisms 30 are also driven by the moving protrusions 32 to pivot with respect to the plate-shaped parts 20 (see FIG. 4B). Owing to the restriction (on the radial direction of the belt 10) of the cylindrical frame 40, the plate-shaped parts 20 can be pushed (driven) by the link mechanisms 30 to move further along the direction perpendicular to the axis line C (the second direction), to contract the belt 10 (see FIG. 1B).

It should be noted that the plate-shaped parts 20 in this embodiment can be driven by the link mechanisms 30 to move close to the axis line C of the belt 10 from four directions simultaneously (as the arrows indicate in FIG. 1B). Accordingly, the belt 10 can be contracted and wrapped around the patient's arm in a uniform manner, so that the pressure applied around the patient's arm is more consistent, thereby improving the comfort of the patients and the accuracy of the results of the blood pressure measurement.

Figure 4A:
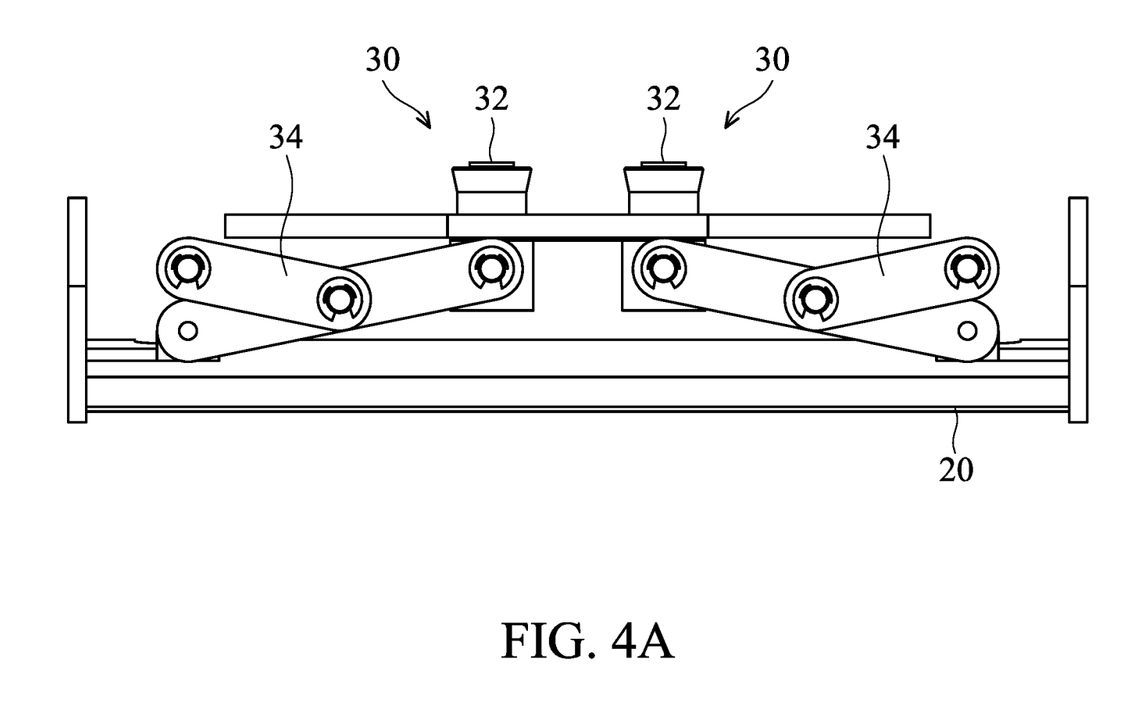
FIG. 4A and FIG. 4B are schematic views showing link mechanisms of the rotating cylinder device in FIG. 1A and FIG. 1B, respectively.
Figure 4B:
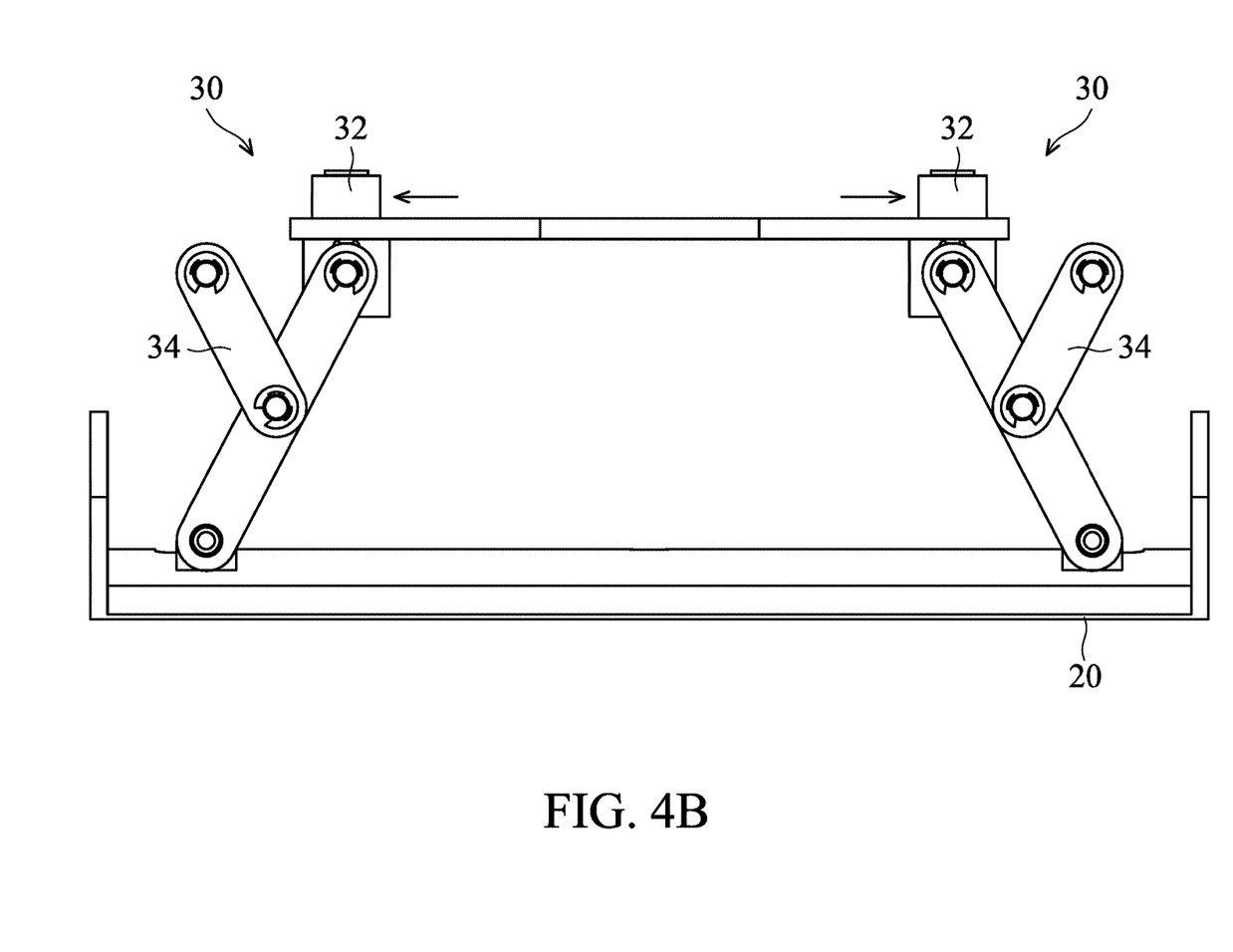

Referring to FIG. 4A and FIG. 4B, in this embodiment, an auxiliary link 34 is further provided between both ends of each of the link mechanisms 30, and both ends of the auxiliary link 34 are coupled to the link mechanism 30 and the cylindrical frame 40 (not shown). The auxiliary link 34 can make the link mechanism 30 pivot more smoothly with respect to the corresponding plate-shaped part 20.

Figure 5:
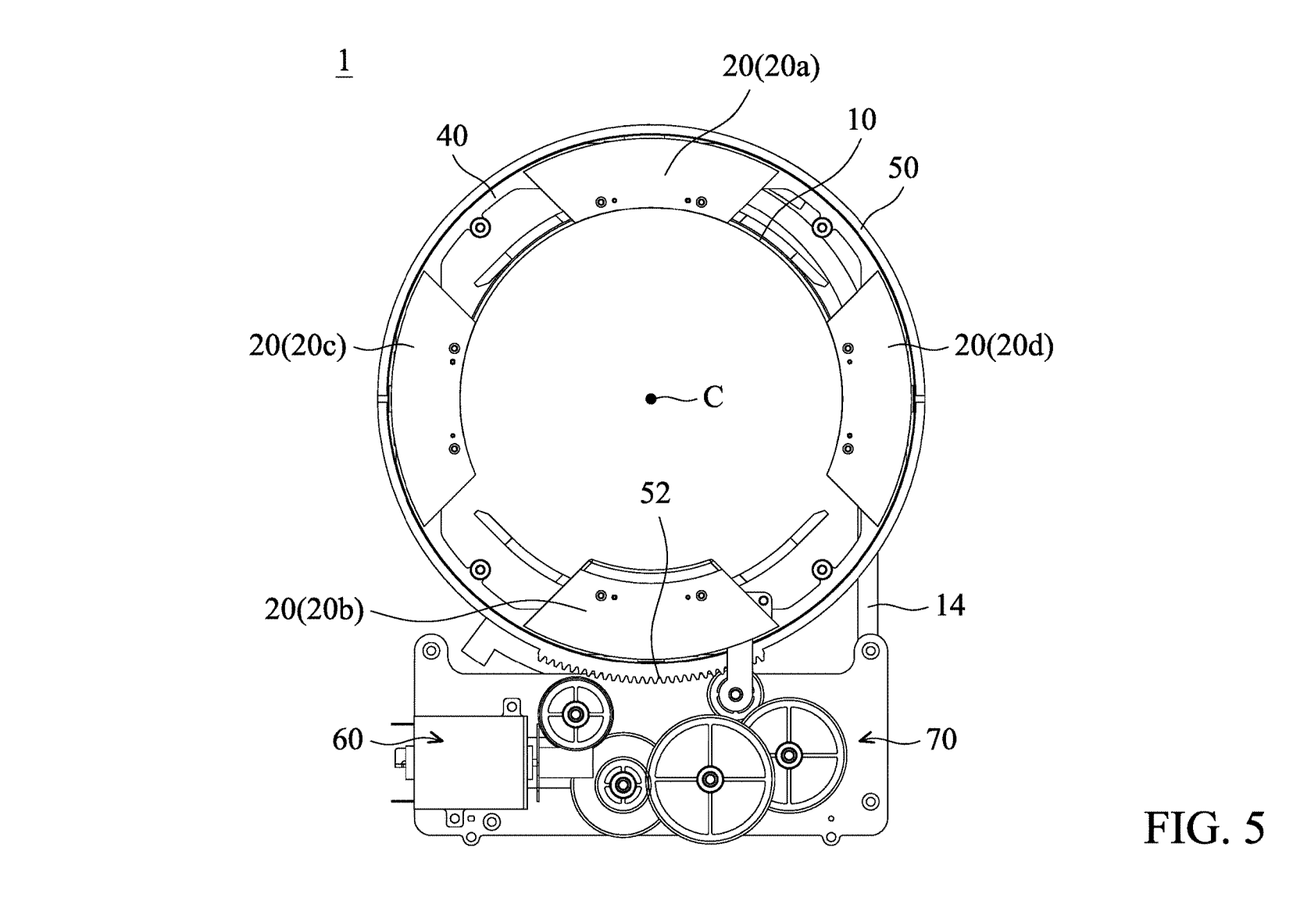
FIG. 5 is a schematic view showing a rotating cylinder device in accordance with an embodiment of the invention including a driving motor and a driving gear set.

Referring to FIG. 5, a rotating cylinder device 1 in accordance with an embodiment of the invention further includes a driving element (e.g. a driving motor 60) and a driving gear set 70. The driving motor 60 is used to drive the cylindrical casing 50 to rotate about the axis line C of the belt 10. The driving gear set 70 is connected to the driving motor 60 and a gear structure (groove 52 on the surface of the cylindrical casing 50.

As mentioned above, the invention provides a rotating cylinder device, including: a belt being substantially cylindrical and having an axis line; a plurality of plate-shaped parts disposed outside the belt and arranged symmetrically across the axis line; a plurality of link mechanisms pivotally connected to the respective plate-shaped parts, wherein one end of each of the link mechanisms is pivotally connected to one of the plate-shaped parts and the other end is provided with a moving protrusion, wherein the moving protrusions of the link mechanisms are adapted to move along a first direction parallel to the axis line; and a cylindrical casing adapted to rotate about the axis line and coupled to the moving protrusions, wherein when the cylindrical casing rotates about the axis line, the moving protrusions are driven to move along the first direction, and the plate-shaped parts are driven by the link mechanisms to move along a second direction perpendicular to the axis line to contract the belt. With the above structural design, the belt of the rotating cylinder device can be contracted and wrapped in a uniform manner, so that the pressure applied around the patient's arm is more consistent.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A rotating cylinder device, comprising:
    a belt being substantially cylindrical and having an axis line that is a rotational central line of a cylindrical casing;
    a plurality of plate-shaped parts disposed outside the belt and arranged symmetrically across the axis line;
    a plurality of link mechanisms pivotally connected to the respective plate-shaped parts, wherein one end of each of the link mechanisms is pivotally connected to one of the plate-shaped parts and the other end is provided with a moving protrusion, wherein the moving protrusions of the link mechanisms are adapted to move along a first direction parallel to the axis line; and
    the cylindrical casing adapted to rotate about the axis line and coupled to the moving protrusions, wherein when the cylindrical casing rotates about the axis line, the moving protrusions are driven to move along the first direction, and the plate-shaped parts are driven by the link mechanisms to move along a second direction perpendicular to the axis line to contract the belt.

2. The rotating cylinder device as claimed in claim 1, wherein when the plate-shaped parts move along the second direction, the plate-shaped parts go from an expanded state to a contracted state, and a distance between each of the plate-shaped parts and the axis line in the expanded state is farther than a distance between each of the plate-shaped parts and the axis line in the contracted state.

3. The rotating cylinder device as claimed in claim 1, further comprising a cylindrical frame disposed between the cylindrical casing and the plate-shaped parts, wherein the moving protrusions pass through the cylindrical frame and are coupled to the cylindrical casing.

4. The rotating cylinder device as claimed in claim 3, wherein the other end provided with the moving protrusion of each of the link mechanisms is movably connected to the cylindrical frame.

5. The rotating cylinder device as claimed in claim 4, wherein the cylindrical frame has a plurality of guide tracks thereon for guiding the moving protrusions as the moving protrusions move along the first direction.

6. The rotating cylinder device as claimed in claim 5, wherein the cylindrical casing has a plurality of oblique grooves thereon, the oblique grooves being coupled to the moving protrusions, and the extension directions of the oblique grooves are different from those of the guide tracks.

7. The rotating cylinder device as claimed in claim 6, further comprising a driving element for driving the cylindrical casing to rotate about the axis line, and the moving protrusions can be driven by the oblique grooves and guided by the guide tracks to move along the first direction parallel to the axis line.

8. The rotating cylinder device as claimed in claim 4, wherein an auxiliary link is further provided between both ends of each of the link mechanisms, and both ends of the auxiliary link are coupled to the link mechanism and the cylindrical frame.

9. The rotating cylinder device as claimed in claim 1, further comprising a driving element for driving the cylindrical casing to rotate about the axis line.

10. The rotating cylinder device as claimed in claim 9, further comprising a driving gear set connected to the driving element and a gear structure on a surface of the cylindrical casing.

11. A rotating cylinder device, comprising:
    a belt being substantially cylindrical and having an axis line;
    a plurality of plate-shaped parts disposed outside the belt and arranged symmetrically across the axis line;
    a plurality of link mechanisms pivotally connected to the respective plate-shaped parts, wherein one end of each of the link mechanisms is pivotally connected to one of the plate-shaped parts and the other end is provided with a moving protrusion, wherein the moving protrusions of the link mechanisms are adapted to move along a first direction parallel to the axis line;
    a cylindrical casing adapted to rotate about the axis line and coupled to the moving protrusions, wherein when the cylindrical casing rotates about the axis line, the moving protrusions are driven to move along the first direction, and the plate-shaped parts are driven by the link mechanisms to move along a second direction perpendicular to the axis line to contract the belt; and
    a cylindrical frame disposed between the cylindrical casing and the plate-shaped parts, wherein the moving protrusions pass through the cylindrical frame and are coupled to the cylindrical casing.

12. The rotating cylinder device as claimed in claim 11, wherein when the plate-shaped parts move along the second direction, the plate-shaped parts go from an expanded state to a contracted state, and a distance between each of the plate-shaped parts and the axis line in the expanded state is farther than a distance between each of the plate-shaped parts and the axis line in the contracted state.

13. The rotating cylinder device as claimed in claim 11, wherein the other end provided with the moving protrusion of each of the link mechanisms is movably connected to the cylindrical frame.

14. The rotating cylinder device as claimed in claim 13, wherein the cylindrical frame has a plurality of guide tracks thereon for guiding the moving protrusions as the moving protrusions move along the first direction.

15. The rotating cylinder device as claimed in claim 14, wherein the cylindrical casing has a plurality of oblique grooves thereon, the oblique grooves being coupled to the moving protrusions, and the extension directions of the oblique grooves are different from those of the guide tracks.

16. The rotating cylinder device as claimed in claim 15, further comprising a driving element for driving the cylindrical casing to rotate about the axis line, and the moving protrusions can be driven by the oblique grooves and guided by the guide tracks to move along the first direction parallel to the axis line.

17. The rotating cylinder device as claimed in claim 13, wherein an auxiliary link is further provided between both ends of each of the link mechanisms, and both ends of the auxiliary link are coupled to the link mechanism and the cylindrical frame.

* * * * *